United States Patent [19]

Dörre et al.

[11] Patent Number: 4,538,306
[45] Date of Patent: Sep. 3, 1985

[54] IMPLANTABLE ELBOW JOINT

[75] Inventors: Erhard Dörre, Plochingen; Peter Prüssner, Dietzenbach; Ludwig Zichner, Frankfurt am Main, all of Fed. Rep. of Germany

[73] Assignee: Feldmühle Aktiengesellschaft, Duesseldorf, Fed. Rep. of Germany

[21] Appl. No.: 506,687

[22] Filed: Jun. 22, 1983

[30] Foreign Application Priority Data

Jun. 26, 1982 [DE] Fed. Rep. of Germany ....... 3223925

[51] Int. Cl.³ ............................................... A61F 1/04
[52] U.S. Cl. ................................... 623/20; 128/92 C; 623/18
[58] Field of Search ..................... 3/1.9, 1.91, 1.911; 128/92 C

[56] References Cited

U.S. PATENT DOCUMENTS

| 3,924,275 | 12/1975 | Heimke et al. | 3/1.913 |
| 4,024,588 | 5/1977 | Janssen | 3/1.91 |
| 4,242,758 | 1/1981 | Amis et al. | 3/1.91 |
| 4,259,752 | 4/1981 | Taleisnik | 3/1.91 |
| 4,332,037 | 6/1982 | Esformes et al. | 3/1.91 |

FOREIGN PATENT DOCUMENTS 1537479 12/1978 United Kingdom ................... 3/1.91

Primary Examiner—Richard J. Apley
Assistant Examiner—David Isabella
Attorney, Agent, or Firm—Toren, McGeady, Stanger, Goldberg & Kiel

[57] ABSTRACT

An implantable elbow joint for connecting the upper arm and the forearm includes an axially extending sleeve of C-shape transverse cross-section, a cylindrical member engageable within the sleeve, and a connecting member implantable in the ulna and engageable with the cylindrical member in the sleeve. The sleeve embraces the trochlea of the humerus through an angle of more than 180° about the sleeve axis and also serves as the abutment for supporting the radius. The sleeve has a slot extending in the radial and the circumferential directions. At least in the region of the slot, the internal surface of the sleeve is formed by a cylindrically shaped surface. A cylindrically shaped sliding member is supported in the sleeve in the region of the slot. An elongated shaft is arranged to be inserted into the ulna with one end projecting out of the ulna and extending through the slot into the sliding member.

12 Claims, 4 Drawing Figures

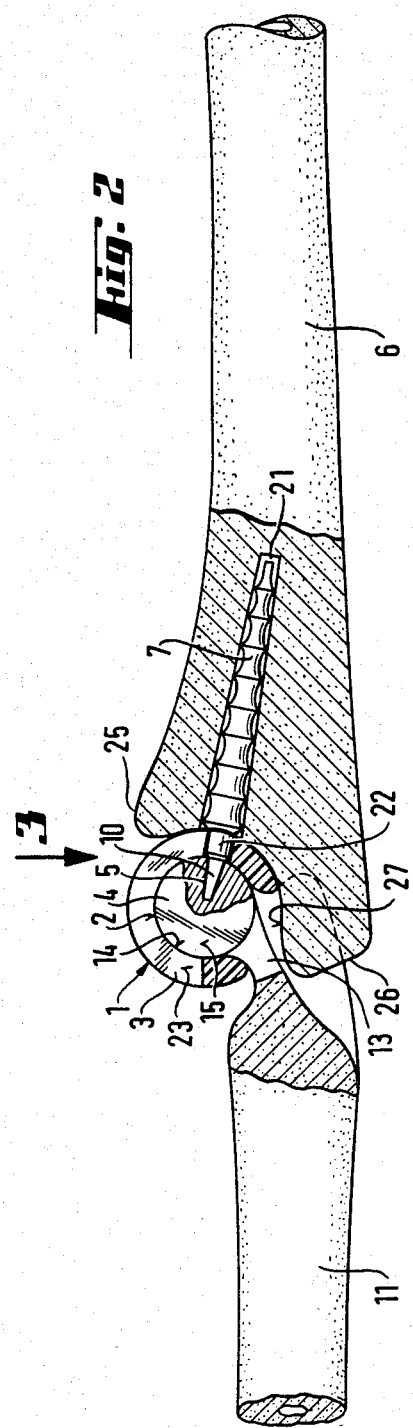

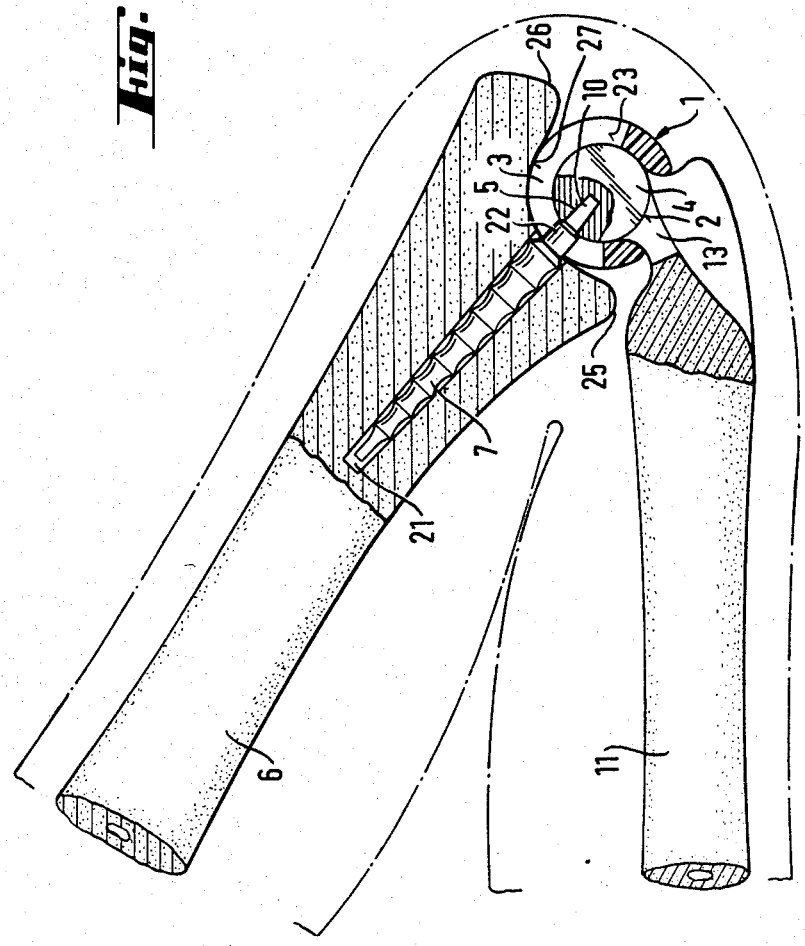

IMPLANTABLE ELBOW JOINT

SUMMARY OF THE INVENTION

The present invention is directed to an implantable elbow joint for connecting the upper arm and the forearm and it is made up of a sleeve having a C-shaped transverse cross-section for embracing the trochlea of the humerus at an angle of more than 180° and also serving as the abutment for supporting the radius, and a connecting member or shaft which is implantable in the ulna.

Elbow joints for replacing the entire joint, that is, where a resection of the entire joint area is required, are known from German Auslegeschrift No. 20 07 214 and German Offenlegungsshrift No. 23 51 912. It is desirable, as much as is possible, to avoid the replacement of the entire elbow joint and to retain as much of the bones of the elbow joint as is possible, to provide the possibility of retreating in the event of further bone involution or disease.

Accordingly, it has been suggested in German Offenlegungsschrift No. 23 59 627 to cut or work the trochlea of the humerus so that a cap can be fastened on it using acrylic resin cement. The cap embraces the resected trochlea and has on its outer surface a spherical portion and a cylindrical portion. The spherical portion is connected to a ball socket which has a mandrel projection, the socket is inserted into the radius whose head has been resected and a cylindrical socket is cemented into the ulna. When bone cements harden, however, temperatures are generated which are so high that the bone structure may be damaged. Therefore, if possible, anchoring by means of bone cement should be avoided.

In German Offenlegunsschrift No. 28 23 406 there is a description of an artificial elbow joint in which the trochlea is embraced by a C-shaped upper arm component of stainless steel having a cylindrical inner region with recesses or roughened areas enabling the component to be connected by bone cement to the resected trochlea. The upper arm component has three spherical portions which correspond essentially to the shape of the trochlea. The end of the trochlea is also resected and provided with a saddle-shaped joint surface lined with plastics material. This joint surface slides on the upper arm component.

In accordance with the present state of the art, it is always necessary to fasten one joint component, such as the trochlea, to the humerus by means of bone cement.

Therefore, it is the primary object of the present invention to provide an implantable elbow joint which does not have the disadvantages of the prior art and ensures a secure connection between the upper arm and the forearm while maintaining the two physiological possibilities of movement of the elbow joint, that is, bending and turning, even when the ligaments are damaged. Further, the implantable elbow joint requires as little bone resection as possible so that the possibility of a subsequent or later operation is available. The present invention facilitates the use of new, highly wear-resistant materials which do not have any disadvantages of previous artificial elbow joints where metal used as a sliding member led to abrasion and the development of toxic metal dust and also to a loosening of the connection with the bone. Moreover, the structural design of the joint makes its use easier for the operating surgeon.

These objects cannot be achieved by a mere recreation of the natural elbow joint, rather it requires completely new developments with respect to construction and material.

In accordance with the present invention, an implantable elbow joint for connecting the upper arm and the forearm includes a sleeve having a C-shaped transverse cross-section for embracing the trochlea of the humerus over an angle of more than 180° and also serving as the abutment for supporting the radius, and a connecting piece which is implantable in the ulna, wherein the following features are combined in accordance with the invention in a novel manner:

The sleeve has a radially and circumferentially extending slot, the inner wall of the sleeve forms an internal cylindrically shaped surface at least in the region of the slot, a cylindrically shaped sliding member is supported within the sleeve in the region of the slot, and an elongated shaft is arranged to be anchored in the ulna and has one end projecting from the ulna so that it can extend through the slot and engage in the sliding member located within the sleeve.

The characteristic features of the invention are the sliding member supported in the sleeve and the slot formed in the sleeve. As a result, the following functions are met and advantages are obtained in a superior manner:

1. The sliding member provides the connection between the upper arm and the forearm as a result of its support in the sleeve and in a corresponding recess in the trochlea and by means of the projection of the shaft extending through the slot.
2. The sliding member absorbs the hinged movement, with the particular advantage that the sliding member subjected to wear is located inside the sleeve. This location is contrary to the natural joint in which the hinge movement takes place on the outer surface of the trochlea against the corresponding opposite surface at the end of the ulna (*incisura trochlearis*).

Another advantage of this structural feature is that, if wear occurs in the incisura trochlearis due to disease, a replacement is not required because the function of the hinge movement is assumed by the sleeve and the sliding member.

3. This elbow joint can be implanted without the use of cement because the interaction of the sleeve and the sliding member affords a simple and secure connection.
4. The arrangement of the elbow joint is operatively simple and safe and retains, as much as is possible, the natural substance of the elbow joint. Only the trochlea is cut in accordance with the shape and dimensions of the internal cylindrical shaped surface of the sleeve, an intermediate piece of the trochlea is removed for inserting the sliding member, the sliding member is inserted and, subsequently, the sleeve is slipped or slid onto the prepared trochlea and the sliding member.

Furthermore, the turning movement of the elbow joint is maintained in a natural manner so that one end portion of the sleeve which is provided with a spherical shape, assumes the corresponding function of this portion of the trochlea, that is, the capitulum humeri, and is in sliding engagement with the head of the radius, that is, the caput radii.

5. Another substantial advantage of the implantable elbow joint of the present invention resides in that the construction is especially suitable for the material, particularly when implant members are used which are made solely from or with the use of sintered hard materials. Sintered hard materials, particularly sintered aluminum oxide, are distinguished by high wear resistance and excellent frictional properties. Such material is of an extraordinary hardness, almost similar to that of diamond, so that their treatment is very expensive and manufacture in accordance with the complicated shapes of human bone would be very expensive. Therefore, when these materials are used, it is desirable to employ uniform, simple geometric shapes which can be obtained with conventional tools and can be ground and polished in a conventional manner. The construction of the inner surface of the sleeve as an internal cylindrically shaped surface and of the sliding member as a simple cylinder are effective in meeting this requirement.

Although the implantable elbow joint may be formed of materials used previously in such joints, such as, metal or plastics material, however, it is particularly advantageous as indicated above, to manufacture at least one or both of the sleeve and the sliding member of a sintered hardened material. Aluminum oxide has been found to be particularly suitable because of its great hardness, wear resistance and inert chemical characteristic. An aluminum oxide is preferred which has an $Al_2O_3$ content of at least 99.5% by weight, a density of more than 3.9 and an average grain size of less than 10 $\mu$m. In addition to great chemical strength and wear resistance, such a material is distinguished in that it can be highly polished. This feature is of particular importance, because the cylindrical surfaces which are in sliding engagement with one another or at least the cylindrical surfaces of the hard material members, are preferably polished to an average surface roughness of less than 0.1 $\mu$m.

With regard to wear resistance and frictional behavior, the optimum embodiment is an implantable elbow joint in which both the sleeve and the sliding member are formed of sintered aluminum oxide in particular because, if body fluid is present as is the case at the elbow joint, aluminum oxide on aluminum oxide has an excellent friction behavior and practically no abrasion occurs which, if it would occur, would be compatible with the body and would not have the disadvantages of the metals used in the past.

Another effective embodiment of the implantable elbow joint embodying the present invention involves the formation of the sliding member from a high density polyethylene with the sleeve formed of sintered aluminum oxide. The combination of materials of polyethylene and sintered aluminum oxide is also distinguished by extremely good friction behavior and low wear.

Because of its greater capability for absorbing bending loads, metal is preferred as the material for the connecting element or shaft, that is, the member which is anchored in the ulna and extends at its free end through the slot in the sleeve into the sliding member. Titanium alloys and alloys of chromium, nickel, cobalt an molybdenum have been found to be particularly suitable. It would also be possible to form the shaft of carbon fiber materials and polyethylene.

A particularly important feature of the implantable elbow joint is the connection of the end of the shaft with the sliding member. It has been found particularly suitable to provide the free end of the shaft, that is the end extending out of the ulna, with a frusto-conically shaped part engageable into a corresponding frusto-conical bore in the sliding member so that a secure connection is achieved in a self-locking manner. The frusto-conical part preferably has a taper ratio in the range of 1:10 to 1:20. In particular, when a sintered aluminum oxide sliding member is used, the receiving frustoconical bore in the sliding member probably has a greater roughness, preferably with an average roughness value Ra of between 0.5 and 3 $\mu$m, so that the frusto-conical bore, due to its hardness and roughness, acts on the frusto-conically shaped end part of metal so as to deform it. This is particularly advantageous because sintered aluminum oxide is sensitive to tension load and these deforming forces absorb the bursting or breaking forces on the sliding member.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described preferred embodiments of the invention.

BRIEF DESCRIPTION OF THE DRAWING

In the drawing:

FIG. 2 is a side view, partly in section, illustrating the elbow joint implanted in the upper arm and the forearm;

FIG. 3 is a view taken in the direction of the arrow 3 in FIG. 2; and

FIG. 4 is a side view, partly in section, illustrating the implantable elbow joint in the bent position within the arm.

DETAILED DESCRIPTION OF THE INVENTION

Figure 1:
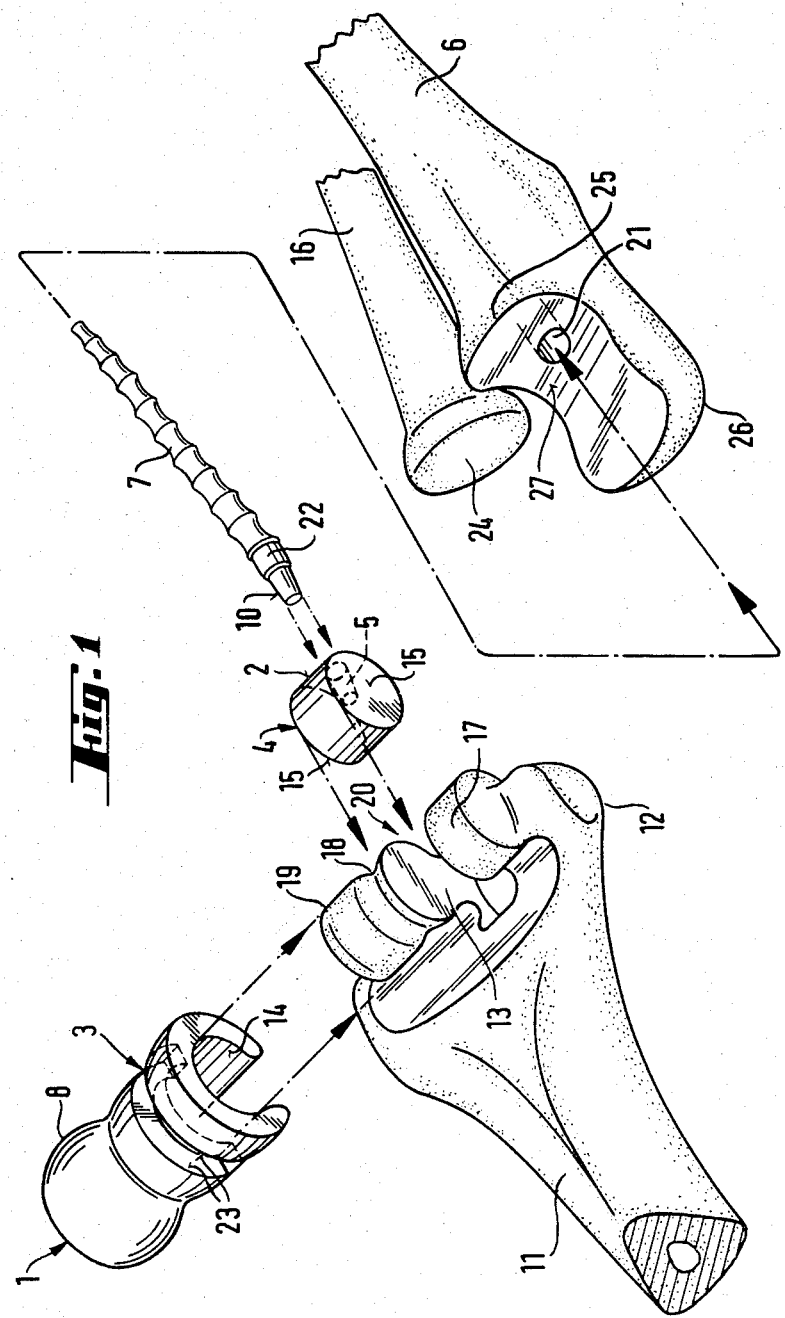
FIG. 1 is an exploded view of the individual parts of the implantable elbow joint embodying the present invention illustrated in relation to the humerus, ulna and radius.

The implantable elbow joint of the present invention consists of a sleeve 1, a sliding member 4, and an elongated shaft 7. As can be seen in the drawing, the axially extending sleeve 1, is not entirely closed around its circumference, rather the sleeve wall extends only through an angle of about 270° so that it can be slid onto the trochlea 17 of the humerus 11. In the region of the sleeve intended for sliding engagement with the head 24 of the radius 16, the sleeve 1 has a spherically shaped portion 8 which is preferably polished to keep the friction low relative to the head 24. With regard to shape and dimension, the spherical portion substantially corresponds to the capitulum humeri 19 prior to resection. As illustrated, the head 24 is kept in its natural configuration, that is, if it has not been destroyed by disease or accident. If the head has been destroyed, or if it can be seen that the disease may extend in the near future to the head 24, the head may be advantageously replaced by an appropriate implant.

The part of the sleeve 1 adjacent to the spherical part 8 is essentially cylindrically shaped and includes a slot 3 extending in the radial direction through the sleeve and also in the circumferential direction. The slot extends preferably for about 120° in the circumferential direction of the sleeve. A projection 22 on the end of the shaft 7 which extends outwardly from the ulna 6, extends through the slot 3. The diameter of the projection 22 is slightly smaller than the width of the slot 3, that is, the dimension of the slot in the axial direction of the sleeve. The shaft 7 has rib-shaped thickened sections along its length which aid in anchoring the shaft in a bore 21 in the ulna 6. When the arm is moved, the projection 22 slides along the side surfaces 23 of the slot 3. To obtain low friction and no abrasion in this situation, the side surfaces 23 and the surface of the projection 22 are preferably polished. At the end of the shaft 7 projecting outwardly from the ulna 6, next to the projection 22, there is a frusto-conically shaped end part 10 with a taper ratio in the range of 1:10 to 1:20.

Sliding member 4 is cylindrically shaped and its length or axial dimension is at least twice the width of the slot 3, that is the dimension of the slot in the axial direction of the sleeve 1. When the elbow joint is implanted, the sliding member 4 is supported within the interior of the sleeve and is in sliding engagement with it. Accordingly, the diameter of the sliding member 4 corresponds substantially to the inside diameter of the sleeve 1 so that the polished outer surface 2 of sliding member 4 is in sliding engagement with the interior cylindrically shaped surface 14 of the sleeve 1, and the cylindrically shaped surface 14 is also polished. The axial length of the sliding member 4 is at least twice the width of the slot 3, as mentioned above, so that a secure guidance of the sliding member within the sleeve is ensured.

When the implantation is performed, a recess 13 is cut out of the trochlea 17 by a side milling cutter. The width of the recess 13 corresponds to the axial length of the sliding member 4. Since the end faces 15 of the sliding member 4 are in sliding and frictional contact with the side surfaces of the recess 13, preferably, the end faces 15 are also polished.

The ulna 6 is resected in the region of the original joint surface, that is, in the coronoid process 25 and the olecranon 26, in a manner corresponding to the cylindrical outer surface of the sleeve in this region, so that an arch-shaped recess 27 is formed in the end of the ulna 6.

Implantation is performed as follows:

First, the trochlea 17 is cut so that it has the shape of a cylinder. It is not necessary to cut the entire trochlea, but, as illustrated in FIG. 1, an uncut region 18 may remain which forms in the trochlea 17 the transition between the prepared capitulum humeria and the prepared condylen 12. A recess 13 is cut on the trochlea 17 by a side milling cutter with the width of the recess 13 corresponding to the axial length of the sliding member 4. As indicated by arrow 20, the sliding member 4 is inserted into the recess 13 so that the frusto-conically shaped bore 5 faces away from the humerus 11.

As illustrated by arrows in FIG. 1, the sleeve is slid from the side onto the prepared trochlea 17 and the sliding member 4 which is inserted in the recess 13. The connection of the ulna 6, into which one end of the shaft 7 is inserted, is effected in a simple manner by passing the projection 22 through the slot 3 and inserting the frusto-conically shaped part 10 on the end of the shaft 7 into the frusto-conically shaped bore 5 located in the sliding member 4.

While specific embodiments of the invention have been shown and described in detail to illustrate the application of the inventive principles, it will be understood that the invention may be embodied otherwise without departing from such principles.

We claim:

1. An implantable elbow joint for connecting the upper arm and the forearm, comprising an axially extending sleeve having a C-shaped cross-section transversely of the axial direction thereof for embracing the at least partly resected trochlea of the humerus with the contact extending about the axis of said sleeve for an angular extent of more than 180°, said sleeve having an inside surface and an outside surface, the outside surface of said sleeve serving as an abutment for supporting the radius, and a connecting member implantable in the ulna, wherein the improvement comprises that said sleeve being mechanically connectible to the trochlea, said sleeve having a slot extending in the radial direction of the sleeve from the inside surface to the outside surface thereof and being elongated in the circumferential direction thereof, the inside surface of said sleeve defines an interior cylindrically shaped surface at least in the region of said slot and extending in the axial direction of said sleeve at least slightly beyond the opposite sides of said slot, an axially extending cylindrically substantially disc shaped sliding member is supported in said sleeve in the region of said slot and between resected surfaces of said trochlea and in sliding contact with said cylindrically shaped surface and said respected surfaces of said trochlea, said sliding member has the axial dimension greater than the dimension of said slot in the axial direction of said sleeve, and said connecting member comprises an elongated shaft having a first end and a second end with the first end arranged to extend into and to be mechanically anchored within the ulna and the second end being arranged to project out of the ulna through said slot and into closely fitting engagement within said sliding member.

2. An implantable elbow joint, as set forth in claim 1, wherein the axial length of said cylindrically shaped sliding member is at least twice the width of said slot extending in the axial direction of said sleeve.

3. An implantable elbow joint, as set forth in claim 1, wherein the inside surface of said sleeve is polished at least in the regions thereof adjoining said slot.

4. An implantable elbow joint, as set forth in claim 3, wherein the outer circumferentially extending surface of said sliding member is polished.

5. An implantable elbow joint, as set forth in claim 1, wherein the end faces of said sliding member extending transversely of the axial direction thereof are polished.

6. An implantable elbow joint, as set forth in claim 1, wherein said sliding member has a conically shaped bore in the circumferential surface thereof and the second end of said shaft has a correspondingly conically shaped part for engagement in said conically shaped bore of said sliding member.

7. An implantable elbow joint, as set forth in claim 1, wherein said sleeve has approximately the same wall thickness over its axial length.

8. An implantable elbow joint, as set forth in claim 1, wherein at least one of said sleeve and said sliding member is formed of a sintered hard material.

9. Implantable elbow joint, as set forth in claim 8, wherein said sintered hard material is aluminum oxide having an $Al_2O_3$ content of at least 99.5% by weight, a density of more than 3.9 and an average grain size of less than 10 μm.

10. An implantable elbow joint, as set forth in claim 8, wherein the ones of the cylindrically shaped surfaces of said sliding member and said sleeve disposed in sliding contact with one another and formed of said hard material are polished to an average surface roughness of less than 0.1 μm.

11. An implantable elbow joint, as set forth in claim 8, wherein said sleeve is formed of sintered aluminum oxide and said sliding member is formed of a high density polyethylene.

12. An implantable elbow joint, as set forth in claim 1, wherein said shaft between the first end thereof and a position spaced from the second end thereof has radially outwardly extending thickened sections located in spaced relation, and said thickened sections being arranged to be inserted into the ulna.

* * * * *